United States Patent [19]

Tsuji et al.

[11] Patent Number: 4,496,766
[45] Date of Patent: Jan. 29, 1985

[54] PROCESS FOR PRODUCTION OF α,β-UNSATURATED KETONES

[75] Inventors: Jiro Tsuji, Kamakura; Isao Shimizu, Tokyo, both of Japan

[73] Assignee: Nippon Zeon Co. Ltd., Tokyo, Japan

[21] Appl. No.: 491,380

[22] Filed: May 4, 1983

[30] Foreign Application Priority Data

May 4, 1982 [JP] Japan .................................. 57-74747

[51] Int. Cl.$^3$ .............................................. C07C 45/65
[52] U.S. Cl. ...................... 568/346; 568/388; 560/174; 560/121; 560/126
[58] Field of Search ......................... 568/397, 388, 346

[56] References Cited

U.S. PATENT DOCUMENTS 3,803,242  4/1974  Rothman et al. .................... 568/398

FOREIGN PATENT DOCUMENTS 0017284  10/1980  European Pat. Off. ............ 568/398

OTHER PUBLICATIONS

Tsuda et al., J.A.C.S., vol. 102, pp. 6381–6384, (1980).
Shimizu et al., Tetrahedron Letters, vol. 21, pp. 3199–3202, (1980).

Primary Examiner—James H. Reamer
Attorney, Agent, or Firm—Sherman & Shalloway

[57] ABSTRACT

A process for producing an α,β-unsaturated ketone of the general formula $$R_1-\overset{O}{\underset{\|}{C}}-\underset{\underset{}{|}}{\overset{R_2}{C}}=C\overset{R_3}{\underset{R_4}{\diagdown}}$$

wherein $R_1$ represents a hydrocarbon group, $R_2$ represents an organic group bonded through a carbon-carbon bond, $R_3$ and $R_4$ represent a hydrogen atom or a hydrocarbon group, and $R_1$, $R_2$, $R_3$ and $R_4$ may be linear or may form a ring when taken together in arbitrary combinations, which comprises contacting an α-disubstituted-β-keto acid ester of the general formula $$R_1-\overset{O}{\underset{\|}{C}}-\underset{\underset{R_3}{\diagup}\underset{R_4}{\diagdown}CH}{\overset{R_2}{\underset{|}{C}}}-\overset{O}{\underset{\|}{C}}-O-\underset{\underset{H}{|}}{\overset{H}{C}}-\underset{\underset{R_5}{|}}{C}=\underset{\underset{R_6}{|}}{C}-R_7$$

wherein $R_1$, $R_2$, $R_3$ and $R_4$ are as defined, and $R_5$, $R_6$ and $R_7$ represent a hydrogen atom or a hydrocarbon group, with a catalyst consisting essentially of (a) a compound of a platinum-group metal and (b) and α,ω-alkylenedi(-disubstituted)phosphine.

13 Claims, No Drawings

PROCESS FOR PRODUCTION OF α,β-UNSATURATED KETONES

This invention relates to a new process for producing α,β-unsaturated ketones. More specifically, it relates to a process for producing α,β-unsaturated ketones from α-disubstituted-β-keto acid esters by a new reaction.

Unsaturated ketones such as cyclopentenone derivatives, cyclohexenone derivatives and cyclododecenone derivatives are useful chemical substances in the fields of perfumes, medicines, chemicals, etc.

A conventional method for synthesizing such unsaturated ketones is the isomerization of compounds having a double bond outside a ring, such as alkylidenecyclopentanones (see, for example, Japanese Laid-Open Patent Publication No. 23240/1976). According to this method, the reactivity of the starting compound varies depending upon the type of side chains, and it has virtually been impossible for this method to achieve industrial synthesis of compounds having an unsaturated bond in the side chain, such as alkenylcyclopentenones.

It is an object of this invention therefore to provide a process for synthesizing unsaturated ketones irrespective of the type of side chains of the starting compounds.

Extensive investigations of the present inventors have led to the discovery that a new process involving the use of an allylic ester of an α-disubstituted-β-keto acid as a starting material meets the aforesaid object.

Thus, according to this invention, there is provided a process for producing an α,β-unsaturated ketone of the following general formula [II]

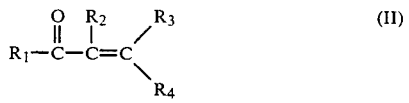

wherein $R_1$ represents a hydrocarbon group, $R_2$ represents an organic group bonded through a carbon-carbon bond, $R_3$ and $R_4$ represent a hydrogen atom or a hydrocarbon group, and $R_1$, $R_2$, $R_3$ and $R_4$ may be linear or may form a ring when taken together in arbitrary combinations, which comprises contacting an α-disubstituted-β-keto acid ester represented by the following general formula [I]

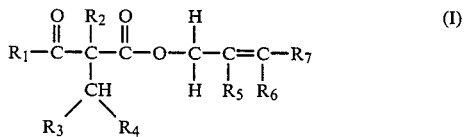

wherein $R_1$, $R_2$, $R_3$ and $R_4$ are as defined above, and $R_5$, $R_6$ and $R_7$ represent a hydrogen atom or a hydrocarbon group, with a catalyst consisting essentially of (a) a compound of a platinum-group metal and (b) an α,ω-alkylenedi(disubstituted)phosphine (to be abbreviated ADP).

In the process of this invention, the allylic ester of an α-disubstituted-β-keto acid represented by formula [I] is used as a starting material. In the formula, $R_1$ is preferably an alkyl group such as a methyl, ethyl, propyl or pentyl group, or an alkylene group bonded to $R_2$, $R_3$ or $R_4$ to form a ring such as a cyclopentane, cyclohexane or cyclododecane ring. $R_2$ is preferably the same alkyl or alkylene group as $R_1$, and may also be an organic group having a polar group such as an alkoxycarbonyl, alkenoxycarbonyl, alkoxyalkyl or alkoxycarbonylalkyl group if it is bonded to the adjacent carbon atom through a carbon-carbon bond. $R_3$ and $R_4$ preferably represent a hydrogen atom or the same alkyl or alkylene group as $R_1$. The substituents $R_1$, $R_2$, $R_3$ and $R_4$ may be taken together in arbitrary combinations to form rings.

Specific examples of compounds of formula [I] are esters formed between α-disubstituted-β-keto acids, such as 1-alkyl-2-oxocyclopentanecarboxylic acids, 1-alkenyl-2-oxocyclopentanecarboxylic acids, 1-alkynyl-2-oxocyclopentanecarboxylic acids, 1-alkyl-2-oxocyclohexanecarboxylic acids, 1-alkenyl-2-oxocyclohexanecarboxylic acids, 1-alkoxycarbonylalkyl-2-oxocyclohexanecarboxylic acids, 1-alkenoxycarbonyl-2-oxocyclohexanecarboxylic acids, 1-alkoxyalkyl-2-oxocyclohexanecarboxylic acids, 1-alkyl-2-oxocyclododecanecarboxylic acids, 1-acetyl-1-cyclopentanecarboxylic acid, α-dialkylacetoacetic acids, and α-dialkyl-β-oxononanoic acids, and allylic alcohols such as allyl alcohol, methallyl alcohol, crotyl alcohol, 2-pentenyl alcohol and 2-ethyl-2-butenol.

These compounds [I] may be synthesized by customary methods. For example, allyl 1-pentyl-2-oxocyclopentanecarboxylate can be synthesized by subjecting diallyl adipate to the Dieckmann condensation to cyclize it to allyl 2-oxocyclopentanecarboxylate, and reacting it with n-pentyl bromide in the presence of potassium carbonate; or by reacting 2-pentylcyclopentanone with allyl chloroformate.

The compounds (a) of a platinum-group metal as one component of the catalyst used in this invention may be any compound which can form a complex with ADP. Preferably, it is a salt or complex of palladium, platinum, rhodium, iridium or ruthenium. Specific examples of such a compound (a) include tris(tribenzylidene acetylacetone) dipalladium (O), tris(tribenzylidene acetylacetone) tripalladium (O), palladium cetate, paladium acetylacetonate, palladium nitrate, palladium sulfate, and palladium chloride. When an inorganic strong acid salt of such a platinum-group metal is used, the reaction is desirably carried out in the presence of a base such as potassium acetate, sodium alcoholates, tertiary amines, etc. Among the platinum-group metal compounds, palladium compounds are preferred because of their reactivity. Of these, zero-valent compounds or divalent organic compounds are especially preferred.

Examples of preferred ADP (b) as the other component of the catalyst are α,β-ethylenedi(diphenyl)phosphine, α,β-ethylenedi(diethyl)phosphine, α,β-ethylenedi(dibutyl)phosphine, α, β-ethylenedi(butyl-phenyl)phospine, α,β-propylenedi(diphenyl)phosphine, and α,β-butylenedi(diphenyl)phosphine. Of these, α,β-ethylenedi(disubstituted)phosphines, especially α,β-ethylenedi(diphenyl)phosphine, are especially preferred. α,β-Ethylenedi(diphenyl)phosphine is a compound represented by the following structural formula.

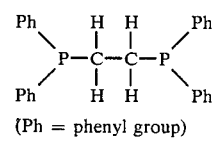

(Ph = phenyl group)

The proportions of the two components (a) and (b) may be properly selected. Usually, component (b) is used in an amount of at least 0.5 mole, preferably 0.7 to 1.5 moles, per mole of component (a). The catalyst composed of the two components (a) and (b) is normally used in such a proportion that the amount of the component (a) is 0.01 to 10 moles per 100 moles of the starting material. The catalyst may be one prepared by reacting the two components in advance. Conveniently, however, the two components are mixed in the reaction system during the reaction to prepare the catalyst in the reaction system.

The reaction in accordance with this invention proceeds as schematically shown below by contacting the starting compound (I) with the catalyst.

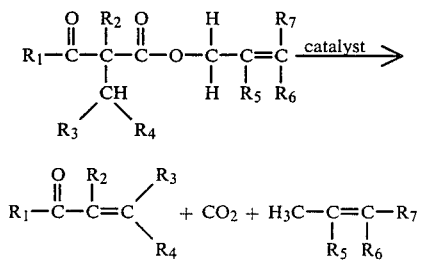

The reaction temperature is usually at least 20° C., preferably 50° to 150° C., and the reaction time is usually 5 minutes to 3 hours.

In order to increase the selectivity of the catalyst for the desired compound, the reaction is preferably carried out in the presence of a diluent. Specific examples of the diluent are acetonitrile, propionitrile, benzonitrile, dimethylformamide, dioxane and benzene. The diluent is used usually in such a proportion that the concentration of the starting material reaches 1 to 50% by weight.

After the reaction, the desired product is separated from the reaction mixture in a customary manner to give an α,β-unsaturated ketone having a high purity. Such unsaturated ketones are used as intermediates for the synthesis of various useful compounds, particularly as intermediates for perfumes and medicines. For example, methyl jasmonate useful as a perfume can be easily synthesized by Michael addition or dimethyl malonate to 2-(2-cis-pentenyl)-2-cyclopenten-1-one synthesized in this invention and subsequent decarboxylation of the addition product.

Thus, by utilizing the new reaction in accordance with this invention α,β-unsaturated ketones can be produced with good efficiency irrespective of whether a side chain to be introduced is saturated or unsaturated.

The following examples illustrate the present invention more specifically. All percentages in these examples are by weight.

EXAMPLE 1

A vessel was charged with 1 mole of allyl 1-pentyl-2-oxocyclopentanecarboxylate of the following formula

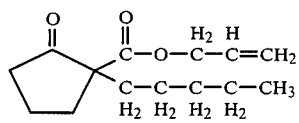

20 moles of acetonitrile, 0.05 mole of palladium acetate and 0.05 mole of α,β-ethylenedi(diphenyl)phosphine, and after these materials were rapidly stirred at room temperature, they were heated to the boiling point of the solvent and reacted under reflux for 30 minutes. After the reaction, the reaction mixture was distilled under reduced pressure in a customary manner to give 2-pentyl-2-cyclopenten-1-one and 2-pentylidenecyclopentanone in a yield of 65% and 13%, respectively. These compounds were identified by using IR, NMR and mass spectroscopic techniques.

EXAMPLE 2

Example 1 was repeated except that allyl 1-(2-pentenyl)-2-oxocyclopentanecarboxylate of the following formula

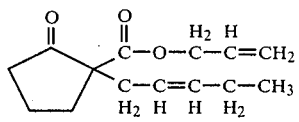

was used as the starting material. As a result, 2-(2-pentenyl)-2-cyclopenten-1-one and 2-(2-pentenylidene)-cyclopentanone were obtained in a yield of 64% and 16%, respectively.

EXAMPLES 3 TO 7

Example 1 was repeated except that each of the compounds indicated in Table 1 was used as the starting material. The results are also shown in Table 1.

TABLE 1

| Example | Starting material | Product | Yield (%) |
|---|---|---|---|
| 3 | Allyl 1-methyl-2-oxocyclohexane-carboxylate | 2-Methyl-2-cyclohexen-1-one | 80 |

TABLE 1-continued

| Example | Starting material | Product | Yield (%) |
|---|---|---|---|
| 4 | 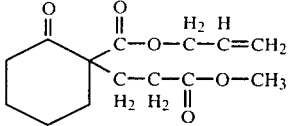 Allyl 1-(methoxycarbonylethyl)-2-oxocyclohexanecarboxylate | 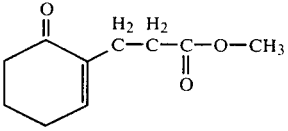 Allyl β-(2-oxo-1-cyclohexenyl)-propionate | 82 |
| 5 | 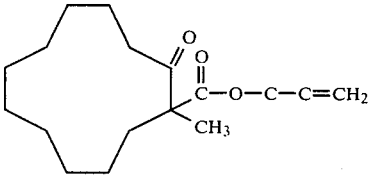 Allyl 1-methyl-2-oxocyclododecanecarboxylate | 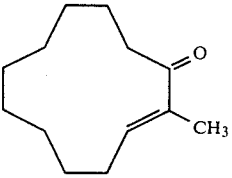 2-Methyl-2-cyclododecen-1-one and 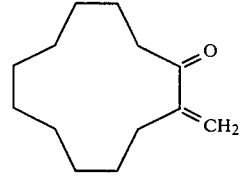 2-Methylenecyclododecanone | 79 |
| 6 | 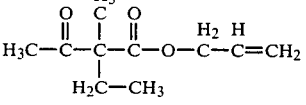 Allyl α-methyl-α-ethyl-acetoacetate | 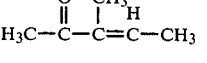 3-Methyl-2-penten-4-one | 50 |
| 7 | 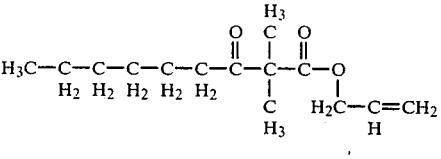 Allyl α-dimethyl-β-oxononanate | 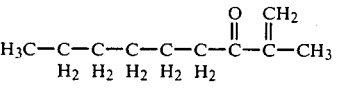 2-Methyl-1-nonen-3-one | 76 |

EXAMPLE 8

Example 1 was repeated except that allyl 1-acetocyclopentanecarboxylate of the following formula was used as the starting material,

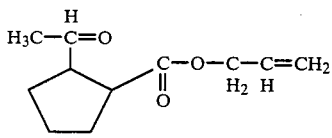

and dioxane was used as a diluent. As a result, 1-aceto-1-cyclopentene of the following formula

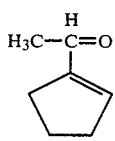

was obtained in a yield of 57%.

EXAMPLE 9

Example 1 was repeated except that palladium acetylacetonate was used instead of palladium acetate. Much the same results as in Example 1 were obtained.

EXAMPLE 10

Example 2 was repeated except that tris(dibenzylideneacetone)dipalladium (O) was used instead of palladium acetate. Much the same results as in Example 1 were obtained.

What is claimed is:

1. A process for producing an α,β-unsaturated ketone of the general formula

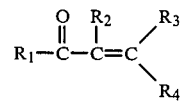

wherein $R_1$ represents an alkyl or alkylene group, $R_2$ represents an alkyl, alkenyl, alkynyl, alkylene, alkoxycarbonyl, alkeneoxycarbonyl, alkoxyalkyl or alkoxycarbonylalkyl group, $R_3$ and $R_4$ represent a hydrogen atom or an alkyl or alkylene group, and $R_1$, $R_2$, $R_3$, and $R_4$ may be linear or may form a ring when taken together in arbitrary combinations, which comprises contacting an α-disubstituted-β-keto acid ester of the general formula

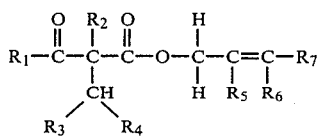

wherein $R_1$, $R_2$, $R_3$ and $R_4$ are as defined, and $R_5$, $R_6$ and $R_7$ represent a hydrogen atom or an alkyl group, said α-disubstituted-β-keto acid ester being an ester formed between a keto acid having not more than 20 carbon atoms and an allylic alcohol having not more than 6 carbon atoms, with a catalyst consisting essentially of (a) a palladium compound and (b) an α,ω-$C_2$-$C_4$ alkylenedi(di-alkyl or phenyl-substituted)phosphine.

2. The process of claim 1 wherein the catalyst consists of 1 mole of component (a) and 0.5 to 1.5 moles of component (b).

3. The process of claim 1 wherein the catalyst is used in such a proportion that the amount of component (a) in the catalyst is 0.01 to 10 moles per 100 moles of the α-disubstituted-β-keto acid ester.

4. The process of claim 1 wherein component (a) of the catalyst is a zero-valent compound of palladium or a divalent organic compound of palladium.

5. The process of claim 1 wherein the alkylene group in component (b) of the catalyst is an ethylene group.

6. The process of claim 1 wherein the keto acid is a 1-substituted-2-oxocycloalkanecarboxylic acid.

7. The process of claim 6 wherein the cycloalkane moiety of the keto acid has 5 to 12 carbon atoms.

8. The process of claim 6 wherein the substituent is an unsaturated hydrocarbon group.

9. The process of claim 1 wherein said contacting is carried out at a temperature of at least 20° C. for a period of 5 minutes to 3 hours.

10. The process of claim 1 wherein said keto acid having not more than 20 carbon atoms is selected from the group consisting of 1-alkyl-2-oxocyclopentanecarboxylic acids, 1-alkenyl-2-oxocyclopentanecarboxylic acids, 1-alkynyl-2-oxocyclopentanecarboxylic acids, 1-alkyl-2-oxocyclohexanecarboxylic acids, 1-alkenyl-2-oxocyclohexanecarboxylic acids, 1-alkoxycarbonylalkyl-2-oxocyclohexanecarboxylic acids, 1-alkenoxycarbonyl-2-oxocyclohexanecarboxylic acids, 1-alkoxyalkyl-2-oxocyclohexanecarboxylic acids, 1-alkyl-2-oxocyclododecanecarboxylic acids, 1-acetyl-1-cyclopentanecarboxylic acid, α-dialkylacetoacetic acids, and α-dialkyl-β-oxononanoic acids, and wherein said allylic alcohol having not more than 6 carbon atoms is selected from the group consisting of allyl alcohol, methallyl alcohol, crotyl alcohol, 2-pententyl alcohol and 2-ethyl-2-butenol.

11. The process of claim 1 wherein said palladium compound (a) is selected from the group consisting of tris-(tribenzylidene acetylacetone) dipalladium (O), tris(tribenzylidene acetylacetone) tripalladium (O), palladium cetate, palladium acetylacetonate, palladium nitrate, palladium sulfate and palladium chloride.

12. The process of claim 1 wherein the phosphine compound (b) is selected from the group consisting of α,β-ethylenedi(diphenyl)phosphine, α,β-ethylenedi(diethyl)phosphine, α,β-ethylenedi(dibutyl)phosphine, α,β-ethylenedi(butylphenyl)phosphine, α,β-propylenedi(diphenyl)phosphine, and α,β-butylenedi(diphenyl)phosphine.

13. The process of claim 1 wherein the phosphine compound (b) is α,β-ethylenedi(diphenyl)phosphine.

* * * * *